United States Patent
Zupkas

[11] Patent Number: 6,106,517
[45] Date of Patent: *Aug. 22, 2000

[54] SURGICAL INSTRUMENT WITH ULTRASOUND PULSE GENERATOR

[75] Inventor: Paul F. Zupkas, San Diego, Calif.

[73] Assignee: Situs Corporation, Solana Beach, Calif.

[ * ] Notice: This patent is subject to a terminal disclaimer.

[21] Appl. No.: 08/939,036

[22] Filed: Sep. 24, 1997

Related U.S. Application Data

[63] Continuation of application No. 08/468,717, Jun. 6, 1995, Pat. No. 5,672,172, which is a continuation of application No. 08/265,666, Jun. 23, 1994.

[51] Int. Cl.$^7$ .................................................. A61B 18/18
[52] U.S. Cl. ............................. 606/20; 606/27; 600/443; 600/462
[58] Field of Search ..................... 606/20–31; 600/437, 600/439, 441–448, 459, 462–464

[56] References Cited

U.S. PATENT DOCUMENTS

| | | | |
|---|---|---|---|
| 3,556,079 | 1/1971 | Omizo | 128/2 |
| 3,911,924 | 10/1975 | Zimmer | 128/303.1 |
| 3,933,156 | 1/1976 | Riggi | 128/303.1 |
| 3,942,530 | 3/1976 | Northeved | 128/303.15 |
| 3,948,269 | 4/1976 | Zimmer | 128/303.1 |
| 3,971,383 | 7/1976 | van Gerven | 128/303.1 |
| 4,018,227 | 4/1977 | Wallach | 128/303.1 |
| 4,022,215 | 5/1977 | Benson | 128/303.1 |
| 4,029,102 | 6/1977 | Barger | 128/303.1 |
| 4,063,560 | 12/1977 | Thomas et al. | 128/303.1 |
| 4,082,096 | 4/1978 | Benson | 128/303.1 |
| 4,146,030 | 3/1979 | Holroyd | 128/303.1 |
| 4,206,609 | 6/1980 | Durenee | 62/6 |
| 4,206,760 | 6/1980 | Davis | 128/303.1 |
| 4,207,897 | 6/1980 | Lloyd et al. | 128/303.1 |
| 4,211,231 | 7/1980 | Rzasa | 128/303.1 |
| 4,236,518 | 12/1980 | Floyd | 128/303.1 |
| 4,249,536 | 2/1981 | Vega | 128/349 |
| 4,249,539 | 2/1981 | Vilkomerson et al. | 128/660 |
| 4,280,499 | 7/1981 | Sguazzi | 128/303.1 |
| 4,345,598 | 8/1982 | Zobac et al. | 128/303.1 |
| 4,377,168 | 3/1983 | Rzasa et al. | 128/303.1 |

(List continued on next page.)

FOREIGN PATENT DOCUMENTS 0 446 645 A1  9/1991  European Pat. Off. .......... A61B 8/12

OTHER PUBLICATIONS

Amertek Medical, Inc. (1998) Sure–Point stepping & stabilizing system for seed implantation http://www.amertek-med.com/image2.htm 6 pgs.

Kapton (1998) High performance films. http://www.kapton-.com/indes.htm 6 pgs.

Flexible Circuitry information (1998) world wide web 9 pgs.

Vernitron (1984) Modern piezoelectric ceramics. PD 9247 1–8.

Blasko, J.C., et al. (1996) Should brachytherapy be considered a therapeutic option in localized prostate cancer? The urologic clinics of north America 23:633–650.

Coleman, D.J., et al. (1986) Therapeutic Ultrasound. Ultrasound in Med. & Biol. 12:633–638.

DeReggi, A.S., et al. (1981) Piezoelectric polymer probe for ultrasonic applications. J. Acoust. Soc. Am. 69:854–859.

Hilaris, B.S. (1997) Brachytherapy in cancer of the prostrate: An historical perspective. Seminars in Surgical Oncology 13:399–405.

(List continued on next page.)

*Primary Examiner*—Cary O'Connor
*Assistant Examiner*—Ryan Carter
*Attorney, Agent, or Firm*—Knobbe, Martens, Olson & Bear, LLP

[57] ABSTRACT

A surgical instrument comprising a probe for insertion into the body of a host and for manipulating the tissues of the host, the probe including an ultrasound transducer element for locating and positioning the probe within the body of the host; and a method for manipulating the tissues of a host using the surgical instrument.

17 Claims, 4 Drawing Sheets

U.S. PATENT DOCUMENTS

| | | | |
|---|---|---|---|
| 4,407,294 | 10/1983 | Vilkomerson | 128/660 |
| 4,412,248 | 10/1983 | Carmen | 358/112 |
| 4,416,281 | 11/1983 | Cooper et al. | 128/400 |
| 4,431,006 | 2/1984 | Trimmer et al. | 128/660 |
| 4,697,595 | 10/1987 | Breyer et al. | 128/660 |
| 4,698,595 | 10/1987 | Röschmann | 324/313 |
| 4,706,681 | 11/1987 | Breyer et al. | 128/642 |
| 4,869,259 | 9/1989 | Elkins | 128/660 |
| 4,946,460 | 8/1990 | Merry et al. | 606/24 |
| 5,010,886 | 4/1991 | Passafaro et al. | 128/660.03 |
| 5,042,486 | 8/1991 | Pfeiler et al. | 128/653 R |
| 5,078,713 | 1/1992 | Varney | 606/27 |
| 5,084,044 | 1/1992 | Quint | 606/27 |
| 5,108,390 | 4/1992 | Potocky et al. | 606/21 |
| 5,147,355 | 9/1992 | Friedman et al. | 606/23 |
| 5,161,536 | 11/1992 | Vilkomerson et al. | |
| 5,174,296 | 12/1992 | Watanabe et al. | 128/662.06 |
| 5,178,148 | 1/1993 | Lacoste et al. | 128/660.03 |
| 5,197,476 | 3/1993 | Nowacki et al. | 128/660.03 |
| 5,199,419 | 4/1993 | Remiszewski et al. | 128/20 |
| 5,211,165 | 5/1993 | Dumoulin et al. | 128/653.1 |
| 5,215,092 | 6/1993 | Wray | 128/660.09 |
| 5,234,004 | 8/1993 | Hascoet et al. | 607/116 |
| 5,243,988 | 9/1993 | Sieben et al. | 128/662.06 |
| 5,247,938 | 9/1993 | Silverstein et al. | 128/662.03 |
| 5,254,116 | 10/1993 | Baust et al. | 606/23 |
| 5,259,384 | 11/1993 | Kaufman et al. | 128/660.01 |
| 5,259,837 | 11/1993 | Van Wormer | 604/96 |
| 5,275,166 | 1/1994 | Vaitekunas et al. | |
| 5,282,472 | 2/1994 | Companion et al. | |
| 5,295,484 | 3/1994 | Marcus et al. | |
| 5,307,816 | 5/1994 | Hashimoto et al. | |
| 5,313,950 | 5/1994 | Ishikawa et al. | 128/662.06 |
| 5,325,860 | 7/1994 | Seward et al. | 128/662.06 |
| 5,370,121 | 12/1994 | Reichenberger et al. | 128/660.02 |
| 5,385,544 | 1/1995 | Edwards et al. | |
| 5,398,690 | 3/1995 | Batten et al. | |
| 5,433,717 | 7/1995 | Rubinsky et al. | 606/20 |
| 5,472,405 | 12/1995 | Buchholtz et al. | |
| 5,474,071 | 12/1995 | Chapelon et al. | |
| 5,531,742 | 7/1996 | Barken | 606/21 |
| 5,564,423 | 10/1996 | Mele et al. | 128/660.02 |
| 5,624,382 | 4/1997 | Oppelt et al. | |
| 5,672,172 | 9/1997 | Zupkas | 606/20 |

OTHER PUBLICATIONS

Holm, H.H. (1997) The history of interstitial brachytherapy of prostatic cancer. Seminars in Surgical Oncology 13:431–437.

Hunt, J.W., et al. (1983) Ultrasound transducers for pulse–echo medical imaging. IEEE Transactions on Biomedical Engineering vol. BMI–30, No. 8 453–481.

Nori, D., et al. (1997) Current issues in techniques of prostrate brachytherapy. Seminars in Surgical Oncology 13:444–453.

Porter, A.T., et al. (1993) Prostate brachytherapy. Cancer supplement 71:953–958.

Schoenwald, J.S., et al. (1983) PVF2 transducers for acoustic ranging and imaging in air. Ultrasonics symposium 577–580.

Watson, L.R. (1997) Ultrasound anatomy for prostate brachytherapy. Seminars in surgical oncology 13:391–398.

White, J.R., et al. (1997) Brachytherapy and breast cancer. Seminars in surgical oncology 13:190–195.

Boring, et al., *CA Cancer Journal for Clinicians*, 42(1):7–26, Jan./Feb. 1993 "Cancer Statistics, 1993".

Fleming, et al., *JAMA*, 269(20):2650–2658, May 26, 1993. "A Decision Analysis of Alternative Treatment Strategies for Clinically Localized Prostate Cancer".

Gage, Andrew, *Gynecology & Obstetrics*, 174:73–92, Jan. 1992.

"Cryosurgery in the Treatment of Cancer".

Klein, Eric, *Cleveland Clinic Journal of Medicine*, 59(4):383–389.

"Prostate Cancer: Current Concepts in Diagnosis and Treatment".

Littrup, et al., *CA Cancer Journal for Clinicians*, 43(3):134–149, May/Jun. 1993.

"The Benefit and Cost of Prostate Cancer Early Detection".

Litwin, et al., *Journal of Urology*, 149:84–88, Jan. 1993.

"Why Do Sicker Patients Cost More? A Charge–Based Analysis of Patients Undergoing Prostatectomy".

Onik, et al., *Radiology*, 168:629–631, 1988 "US Caracteristics of Frozen Prostate".

Meijer, et al., *European Journal of Surgical Oncology*, 18:255–257, 1992 "Cryosurgery for Locally Recurrent Rectal Cancer".

Mettlin, et al., *CA Cancer Journal for Clinicians*, 43(2):83–91, Mar./Apr. 1993 "Trends in Prostate Cancer Care in the United States, 1974–1990: Observations from the Patient Care Evaluation Studies of the American College of Surgeons Commssion on Cancer".

Telang, et al., *Henry Ford Hospital Medical Journal*, 40(1 & 2):108–110 "Radical Surgery in the Treatment of Localized Carcinoma of the Prostate".

Whitmore, Willet, Jr., *JAMA*, 269(20):2676–2677 "Management of Clinically Localized Prostatic Cancer, An Unresolved Problem".

ANTERIOR

POSTERIOR

SURGICAL INSTRUMENT WITH ULTRASOUND PULSE GENERATOR

This application is a continuation of U.S. patent application Ser. No. 08/468,717, filed Jun. 6, 1995, now U.S. Pat. No. 5,672,172, which is a file wrapper continuation of U.S. patent application Ser. No. 08/265,666, filed Jun. 23, 1994.

FIELD OF INVENTION

The present invention relates to the field of medical surgical instruments. More particularly, it relates to a medical surgical probe having an ultrasound transducer operatively incorporated into the tip of the probe. The probe having manipulating means for manipulating tissue within the human body in a minimally invasive manner. The visualization and localization of the probe tip and the tissue manipulation is enhanced by ultrasound pulses generated at the tip of the probe.

DESCRIPTION OF RELATED ART

The development of medical surgical instruments has focused on providing surgeons and physicians with safer and more effective tools to diagnose and treat patients. One area receiving considerable recent attention is the development of tools providing the capability of operating on a patient in a minimally invasive manner. In contrast to conventional surgical methods, these tools reduce morbidity, the time and trauma of surgery, postoperative pain and recovery time. These tools make surgery safer and less costly. Examples of tools developed to operate in this manner include laparoscopic, thoracoscopic, endoluminal, perivisceral endoscopic, and intra-articular joint instruments. The role of minimally invasive surgery in medicine is presented in Minimally *Invasive Surgery,* by J. Hunter, and J. Sackier, New York:McGraw Hill, Inc. 1993, and *Advances in Minimally Invasive Surgery,* New York:New World Press, 1993).

Minimally invasive surgery uses a variety of methods to manipulate tissue within the body. These methods include lasers, electromagnetic energy, mechanical manipulation, and freezing. The freezing of tissue or cryosurgery was practiced as early as 1850 for treating breast and uterine cancers. More recently, cryosurgery has been used in a minimally invasive manner to treat carcinoma of the prostate, breast, colon and other organs. The objective of the physician in treating carcinoma is to effectively destroy all cancer cells in the patient's body. Cancer cells left alive after treatment are future sites for recurrence of the disease.

A major hurdle facing the surgeon or radiologist in using minimally invasive surgical instruments has been the difficulty in visualizing and positioning instruments. Decreasing instrument size and increasing complexity of operations have placed greater demands on the surgeon to accurately identify the position of instruments and details of the surrounding tissue. Visualization is a critical component to the successful use of minimally invasive surgical or diagnostic instruments. In laparoscopic surgery, visualization is accomplished by using fiber optics. A bundle of microfilament plastic fibers is incorporated in the instrument and displays a visible image of the field of interest to the surgeon. The quality of this image directly impact the surgeons ability to successfully manipulate tissue within the patient's body. An overview of laparoscopy is presented in *New Applications in Laparoscopy* by David W. Easter. Other visualization methods include fluoroscopy, magnetic resonance imaging, thermal imaging, and ultrasound.

Ultrasound imaging is based on the reflection of high frequency ultrasound energy from tissue surfaces within the body. Modern B-mode ultrasound imaging systems are capable of noninvasively scanning an area deep within the body and displaying a two dimensional image of the area, typically a transverse or lateral plane relative to the position of the ultrasound scanner (see *Ultrasound Physics and Instrumentation,* D. Hykes, New York:Churchill Livingston, 1985). Reflection of ultrasound energy occurs at tissue interfaces as a result of a mismatch in the acoustic impedance between the tissues. This makes visualization of soft tissues possible, establishing ultrasound imaging as an important tool for visualizing organs and locating and guiding surgical instruments during minimally invasive procedures.

The last two decades have seen tremendous advances in the sophistication of ultrasound imaging technology. Improved signal processing techniques and transducer construction and design have lead to imaging systems that resolve details of internal tissues of under 1 mm. Visualization of the internal structure of organs by B-mode imaging systems improved greatly with the introduction of grey scale imaging in the early 1970s. This method enables different echo amplitudes to be displayed in varying shades of grey. The sophistication of present ultrasound imaging systems has lead to the evolution of ultrasound into a specialty of its own. This specialty focuses on training personnel to operate modern ultrasound systems and interpret and understand ultrasound images.

Ultrasound imaging plays a very important role in the use of cryosurgery to treat carcinoma, tumors, cyts and other soft tissue masses in a minimally invasive manner. The present state of the art in cryosurgery employs the placement of cryoprobes into tissue beneath the surface of the skin through small incisions. Ultrasound imaging is used as the visualization means for guiding and positioning the tip of the cryoprobe beneath the skin surface. The cryoprobe freezes tissue in the region surrounding the probe tip, preventing undesirable damage to tissue contacting the cryoprobe between the skin surface and the cryoprobe tip. The cryoprobe manipulates or destroys tissue by creating a freeze zone or iceball that starts and grows radially from the cryoprobe tip. Ultrasound imaging is used to visualize the extent of the freezing process by displaying the acoustic interface between frozen and nonfrozen tissue.

Although the use of cryosurgery in a minimally invasive manner would not be possible without the visualization provided by ultrasound imaging, there are problems and limitations with present cryosurgical procedures. Two major difficulties the surgeon faces with present cryosurgical procedures are, (1) properly locating the cryoprobe tip in the desired position within a tissue, (2) insuring that all diseased tissue is destroyed while healthy surrounding tissue is not damaged or affected by the freezing process.

The position of the cryoprobe at the start of the freezing process, determines the center of the formation of the iceball. The iceball radiates outward in a spherical pattern. Tissue within the sphere is frozen and destroyed. The objective of the surgeon is to position the cryoprobe tip to maximize the destruction of diseased tissue and preserve healthy surrounding tissue. The cryoprobe tip represents a single point in the two dimensional display created by a B-mode ultrasound imaging system. Identifying and guiding a single point, represented by the cryoprobe tip, in a three dimensional body space using a two dimensional image is a daunting task for even the trained operator.

Visualization of the iceball and its progression are critical steps in validating the destruction of diseased tissue and the safety of surrounding healthy tissues. The interface between the tissue frozen by the cryoprobe and nonfrozen tissue appears as a white border in the CRT display of an ultrasound image of tissue manipulated during a cryosurgical procedure. This border radiates out from the cryoprobe tip in the display of an ultrasound image as the freezing progresses. Because the acoustic impedance of frozen tissue is more than double nonfrozen tissue, little, if any, ultrasound energy is transmitted through the interface. This makes it difficult to visualize areas of nonfrozen tissue within the border of the iceball or in close proximity to the border.

The difficulties with visualizing small objects or areas in the body that are not good reflectors of ultrasound energy is well recognized. Many methods are known in the art of ultrasonography for enhancing the visualization of objects or areas within the body by ultrasound imaging systems (*Diagnostic Ultrasound* by F. Kremkau, Philadelphia:W. B. Saunders Co. 1993 and *Diagnostic Sonography* by A. Fleischer and A. James, Philadelphia: W. B. Saunders 1989). These methods are either passive, enhancing the reflection of ultrasound, or active, generating or receiving an ultrasound pulse, in nature. Two areas where enhancement of visualization has received considerable attention has been tissue biopsy and cardiac catheterization (*Advances in Ultrasound Techniques and Instrumentation,* Well, P. New York; Churchill Livingstone, 1993).

Passively enhancing the visualization of a tissue biopsy needle in an ultrasound image is described in Elkins, U.S. Pat. No. 4,869,259, Echogenically Enhanced Surgical Instrument and Method for Production Thereof. Enhancement is accomplished by roughening a portion of the surface of a needle to improve the scattering or nonspecular reflection of ultrasound energy from the roughened surface. Van Wormer, U.S. Pat. No. 5,259,837, Acoustically Enhanced Catheter, describes the use of coils of metal wire around a portion of a cardiac catheter to enhance scattering of ultrasound energy from that portion of the catheter. Both methods of marking surgical instruments improve visualization by passively enhancing the reflected ultrasound energy and are relatively inexpensive to implement and support. However, both method also depend upon reflection of ultrasound energy, making them liable to visualization problems associated with signal attenuation. In addition, the passive nature of both methods limits the information on surrounding tissue available to the operator in contrast to active marking methods.

U.S. Pat. No. 3,556,079 describes a device generating an ultrasound beam to describe the position of a surgical instrument relative to a blood vessel deep within the body and guide the instrument towards a puncture site on the vessel. The ultrasound beam is transmitted through the instrument towards the vessel. The backscatter of the beam is received by a transducer on the skin surface. The Doppler shift of the beam is measured and converted to an audible sound. The volume of the sound guides the operator in manipulating the instrument to the vessel for puncture. However, the device cannot visualize the exact position of the instrument within the body. It provides a relative position of the instrument in relation to the vessel, making it inappropriate for locating a fixed position within the body. At the same time, this device and method cannot visualize or describe features or status of tissue surrounding the surgical instrument.

The use of an omni-directional ultrasound transducer is described by Vilkomerson, U.S. Pat. No. 4,249,539, Ultrasound Needle Tip Localization System. The transducer, located at the tip of a hollow needle, generates a ultrasound wave or pulse that is sensed by the transducer of a B-mode pulse echo ultrasound imaging system. The signal appears as a point source on the display of the imaging system, revealing the position of the needle tip. Placing the needle in the proper position for tissue sampling, the transducer is removed and tissue is aspirated through the needle for the purpose of testing. This device has the disadvantage of requiring the removal of the ultrasound transducer to allow for aspirating or manipulating tissue. Removing the transducer eliminates the locating method for identifying the probe tip and the ability of using the transducer to provide information on the status of the probe or surrounding tissue during the manipulation process.

The use of ultrasound transducers actively incorporated into a surgical instrument that does not require the removal of the transducer to manipulate surrounding tissue is described by Breyer in U.S. Pat. No. 4,697,595, Ultrasonically Marked Cardiac Catheter. Ultrasonic transducers are permanently embedded within the wall of the lumen of a cardiac catheter. The embedded transducers receive ultrasound pulses from a commonly used B-mode ultrasound imaging system causing the transducers to generate an electrical signal. This electrical signal is processed and incorporated into the display of the imaging system, thereby locating the position of the catheter within the vessel. Although this method does not require the removal of the ultrasound transducer to manipulate tissue, its does depend on receiving ultrasound energy to localize the catheter. This is a disadvantage if the manipulation of tissue by a surgical instrument changes the ultrasound transmission properties of the tissue surrounding the device. This change can block any signal from reaching the device or effect the signal in such a way to render it useless in localizing the device.

A method for locating the tip of a catheter using an ultrasound transducer to transmit a pulse is described in U.S. Pat. No. 5,042,486, Pfeiler, Catheter Locatable with Nonioning Field and Method for Locating Same. The tip transducer, described as an antenna to transmit or receive ultrasound pulses, a non-ionizing form of energy, is coupled with a second series of antennas located on the surface of the skin. The combination of the two series of antennas, one series acting as transmitters and the other series acting as receivers, locate the tip of the catheter by measuring the transit time of the pulses. The location of the tip is superimposed on a radiologically acquired image of the vessel. This image defines the path of the catheter by precisely defining the structure and topology of the vessel in which the catheter is confined to move. The operator can then monitor the real-time movement of the catheter within the vessel using ultrasound without exposing the operator or patient to continuous and potentially harmful ionizing radiation. However, radiologic imaging cannot visualize structural details of soft tissues. This makes the device and method inappropriate for locating a surgical instrument within soft tissue. Without the ability to adequately visualize details of soft tissue structures, it is impossible to identify a single point or position an instrument within a soft tissue mass.

SUMMARY OF INVENTION

In accordance with the present invention, a surgical instrument is provided that overcomes the above-mentioned problems, providing a safer and more effective method for performing minimally invasive surgery. The claimed instrument is a surgical probe adapted for insertion into the body of a patient and includes means for manipulating the tissue of the host. Manipulation means are typically, but not restricted to, a freezing or heating element for destroying diseased or aberrant tissue.

An ultrasound transducer that actively emits ultrasound pulses is operatively incorporated into the instrument. The ultrasound transducer element of the instrument provides a means for locating and positioning the manipulation means within the body of the host or patient. Furthermore, the ultrasound transducer provides a means for visualizing tissue within the target or manipulation zone and identifying variations in the status of the manipulated tissue, i.e. the effect of the manipulation means on said tissue.

The invention further provides a method for manipulating target tissue of a host. The method involves contacting the host with a scanner of an ultrasound imaging system. The scanner operates to create an image of a target zone within target tissue for placing a surgical instrument, the instrument comprising the claimed probe with ultrasound transducer. The ultrasound transducer element of the probe is operatively connected with an ultrasound imaging system. With the aid of the image provided by the scanner with further image input from the ultrasound transducing element, the manipulation means of the probe is guided by an operator into the target zone tissue. The method involves manipulating the tissue in the target zone, and further involves manipulation of the target zone tissue with the aid of images which identify and locate target zone tissue which is destroyed by the step of manipulating the tissue in the target zone.

In use, the claimed method involves using an ultrasound imaging system to create an image of the target zone within the soft tissue for placing a surgical instrument, the instrument comprising the claimed probe with ultrasonic transducer. The imaging system and ultrasonic transducer element of the probe are operatively connected. The image created by the imaging system with further input from the ultrasound transducer in the claimed probe, enables the operator to guide the manipulation means of the probe to a position within the target zone to optimize the destruction of diseased tissue. The method further optimizes the destruction of diseased tissue by enhancing the image or visualization of the manipulated tissue by the claimed probe.

DETAILED DESCRIPTION OF THE INVENTION

Figure 1:
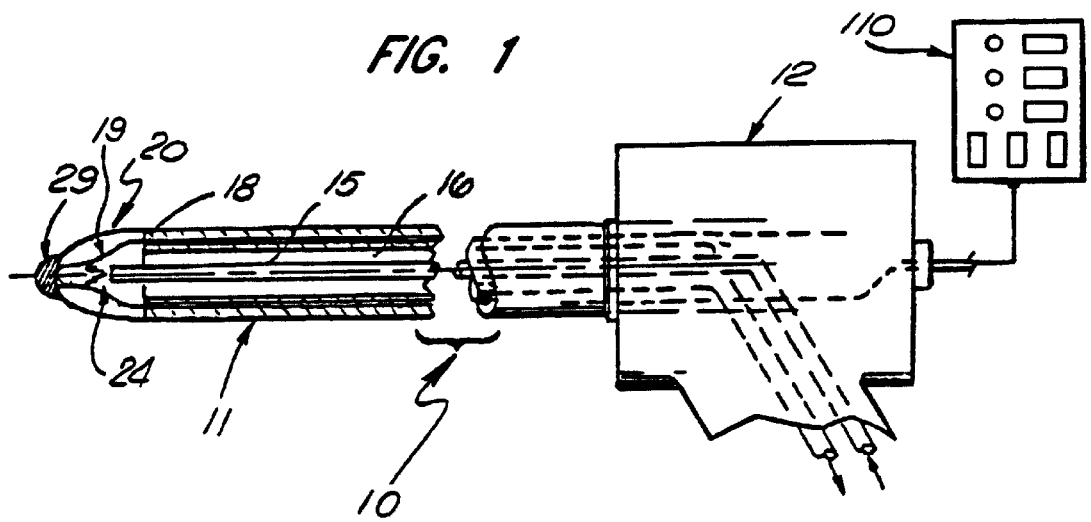
FIG. 1 is a longitudinal cross-section of a surgical instrument in accordance with the present invention portrayed as a cryosurgical probe constructed with an ultrasound transducer at the probe tip.

Objectives of the present invention include providing a surgical instrument that can safely and effectively manipulate tissue in a minimally invasive manner, and a method of manipulating tissues of a host which involves using the claimed surgical instrument. The unique features of the present invention are to provide the surgeon or physician with a means to clearly and easily localize the tissue manipulation portion of the probe and enhance the visualization of the extent and effect of the manipulation process. The present invention is particularly beneficial when the manipulation portion of the instrument is adapted to freezing tissue, but may also be adapted to heat tissue using thermal or electromagnetic energy.

An ultrasound transducer is actively incorporated into the tip of the present invention. This provides the operator (generally a surgeon or physician) an advantage when visualizing the instrument and the manipulation of the surrounding tissue by the probe using an ultrasound imaging system. When used in this manner, the present invention overcomes many of the problems inherent in visualizing surgical instruments during minimally invasive procedures.

In operation, the transducer element of the claimed instrument is made to appear as a point source in the CRT display of a standard commercially available B-mode ultrasound imaging system. This facilitates locating and positioning the manipulating portion of the instrument within the body. The transducer also serves to enhance the visualization of tissue within the zone manipulated by the instrument by emitting ultrasound pulses during the manipulation process.

The ultrasound transducer in the present invention is supported by a system of external electronics that serves to determine when to generate ultrasound pulses and provide the power to drive the transducer. It is well understood in the art of ultrasound imaging that the image of an object created by an imaging system is the result of the reflection of ultrasound pulses or echos from the surface of the object in the scanned area. To visualize and localize an object, the imaging system generates ultrasound pulses and uses the transit time of the returning echos to create an image of the area scanned. The external electronics supporting the present invention serve to determine when to power the transducer to generate pulses that appear as echos of the imaging system pulses or to provide feedback to the imaging system of the transit time of the imaging system pulses. Employing either method, the ultrasound transducer incorporated in the claimed instrument must sense the arrival of the pulses from the imaging system to enable the transducer to appear in the image of the area scanned by the imaging system. The principles governing the design and function of ultrasound imaging systems and the requirements of the external electronics to function with these systems are well understood and documented in the literature (*Ultrasound Physics and Instrumentation* by D. Hykes, New York: Churchill Livingston 1985).

As the instrument manipulates the surrounding tissue, the pulses transmitted by the transducer enhance the visualization of the extent of the manipulation process. In this manner, the present invention improves the safety and efficacy of minimally invasive surgery procedures, in contrast to surgical instruments relying upon the passive reflection of ultrasound pulses from an ultrasound imaging system to visualize the instrument and the extent of the manipulation of tissue by the instrument. In review of prior art presented above, the method for using an actively incorporated ultrasound transducer to identify and guide the manipulation portion of a surgical instrument and enhance the visualization of the extent of the manipulation process is unique.

The claimed surgical instrument is shown in a prefer red embodiment as a cryoprobe in FIG. 1. Shown in cross-section, the cryoprobe 10 possesses a shaft portion 11 and a handle portion 12. The cryoprobe 10 utilizes a typical concentric tube construction for delivery and removal of refrigerant to an expansion chamber 24 at the tip of the cryoprobe 20. Incorporated in the tip of the cryoprobe is an omnidirectional ultrasound transducer 29 with conductors 19 from the transducer to external electronics 110. The ultrasound transducer 29 (available from American Piezo Ceramics, Inc. Mackeyville, Pa.) emits ultrasound pulses, preferably in the range 2–10 MHz. Commercially available transducers are constructed of ceramic materials, typically barium titanate or lead titanate zirconate. The ultrasound transducer 29 is impedance matched at approximately 2–5 ohms to the external electronics 110.

The probe shaft 11 is constructed of three concentric tubes. The inner tube defines an inlet channel 15 for refrigerating fluid through the shaft. The middle tube defines an outlet channel 16 for refrigerating fluid through the shaft. The outer tube forms the cryoprobe shaft 11 and the surface contacting tissue when inserted in the body. The space 17 between the middle and outer tubes is vacuum sealed 18 at the tip of the shaft 20, preventing the space 17 from communicating with inlet 15 or outlet 16 channels. This space serves to insulate the outer tube from the flow of refrigerant except at the tip of the shaft 20.

The refrigerating fluid, typically liquid nitrogen, flows through the inlet channel 15 into the tip expansion chamber 24 and expands, causing a reduction in temperature through a Joules-Thompson effect in the chamber. The expansion of the fluid in the chamber 24 and the insulation of the cryoprobe shaft from the flow of refrigerant, cause tissue surrounding only the tip portion of the cryoprobe shaft to freeze. The zone of frozen tissue radiates outward from the cryoprobe tip, as the refrigerant flows through the expansion chamber 24.

Figure 2:
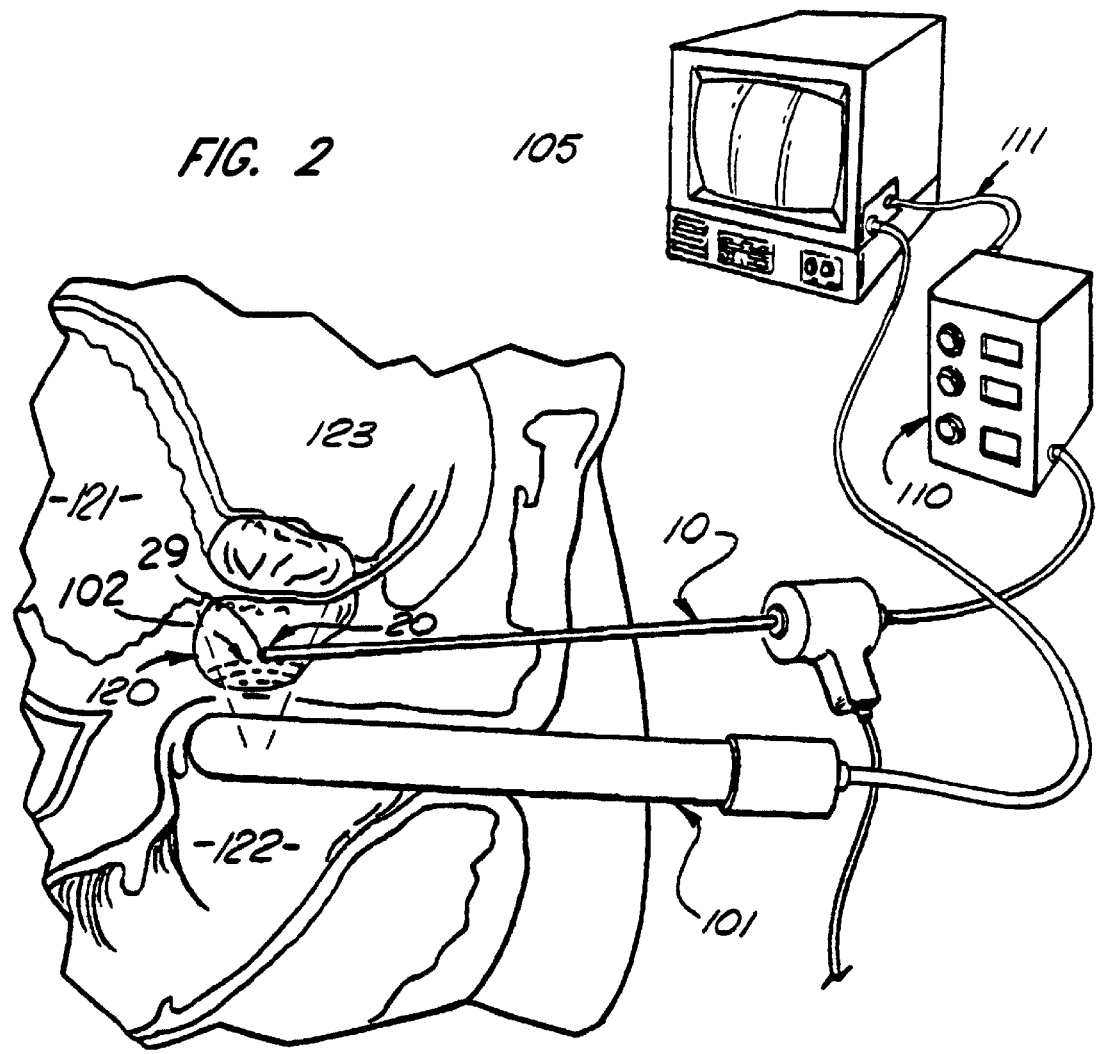
FIG. 2 is a perspective view of the probe placed within the prostate under guidance of an ultrasound imaging system using a scanner placed in the rectum to visualize the prostate.
Figure 3:
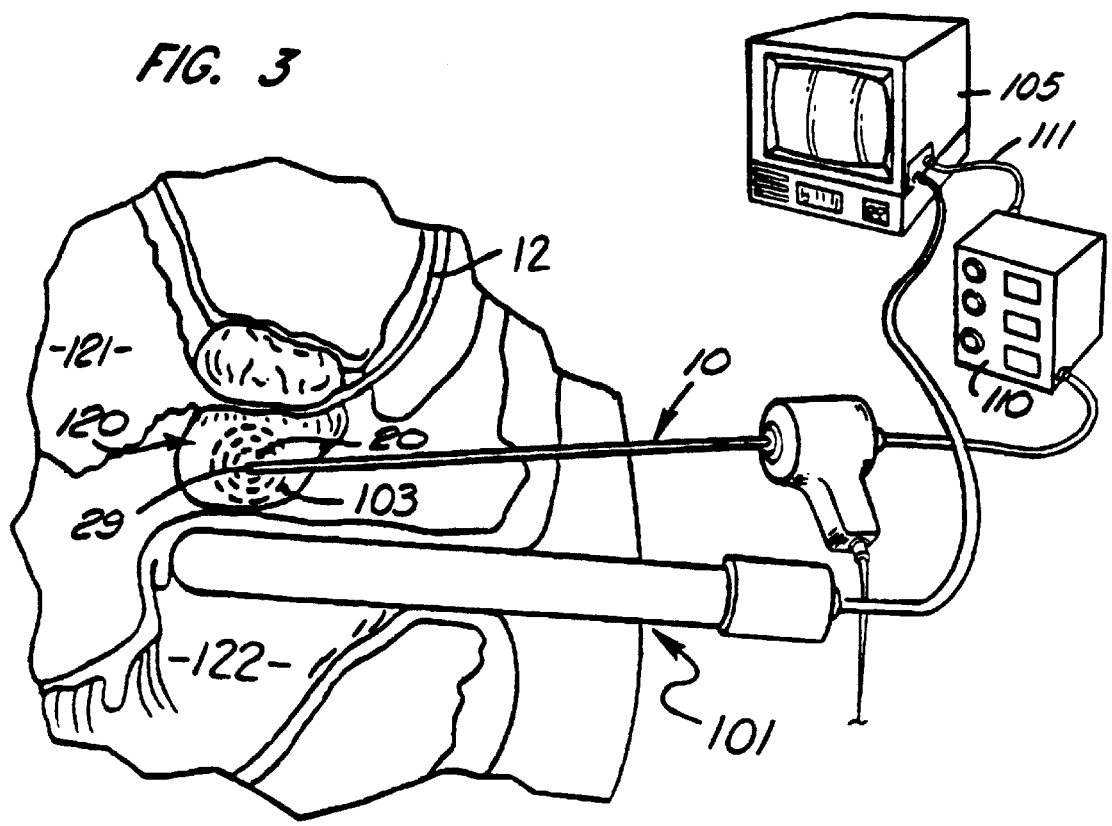
FIG. 3 is a perspective view of the probe generating ultrasound pulses at the probe tip and received by a scanner of an ultrasound imaging system in the rectum to localize the position of the tip of the probe in the prostate.

The pulses emitted by the transducer 29 enhances the visualization of the cryoprobe 10 when placed in an area scanned by a standard medical ultrasound imaging system (available from General Electric Medical Systems, Milwaukee, Wis. or Brauel & Kjaer, Naerum, Denmark). FIG. 2 shows the present invention as a cryoprobe inserted into the prostate gland 120 under the guidance of transrectal ultrasonography (TRUS). The TRUS scanner 101 creates an image of the prostate gland 120, generating ultrasound pulses 102 that are received by the transducer 29 and converted into an electrical signal. The electrical signal is transmitted to external electronics 110. When the electronics 110 determines the pulses were generated by the TRUS scanner 101, it powers the transducer 29 to emit ultrasound pulses. The pulses are generated at the same instant the pulses 102 are reflected by the cryoprobe tip 20, enhancing the strength of the reflected pulses or echos. Shown in FIG. 3, the enhanced echos 103 are received by the TRUS scanner 101 and incorporated into the scan of the area displayed by the imaging system 105.

The enhanced echos 103 localize the cryoprobe tip 20 and the manipulation portion of the cryoprobe, the expansion chamber 24, in the prostate 120 and in relation to healthy tissue surrounding the prostate. Because the echos 103 are displayed real time, the movement of the cryoprobe tip can be viewed. This allows the surgeon or physician to precisely position the cryoprobe as to maximize the destruction of the prostate 120 and the safety of healthy surrounding tissue, such as the bladder 121, rectum 122 or urethra 123.

As heretofore used, ultrasonography provides a method for visualizing the growth of the zone of frozen tissue or iceball. Waves or pulses of ultrasound energy are nearly totally reflected at the interface between frozen and nonfrozen tissue due to the acoustic impedance mismatch between the tissues. The small portion of the pulses transmitted through the interface between frozen and nonfrozen tissue face the same impedance mismatch when reflected back to the imaging system. The result is the imaging system is unable to visualize tissue details within the iceball and can only define the extent of the freezing process from the outside border of the iceball. The present invention uses the transducer 29 to improve the safety and efficacy of the present application by enhancing the visualization of the extent of the freezing process and providing greater definition of tissue within the iceball.

Figure 4:
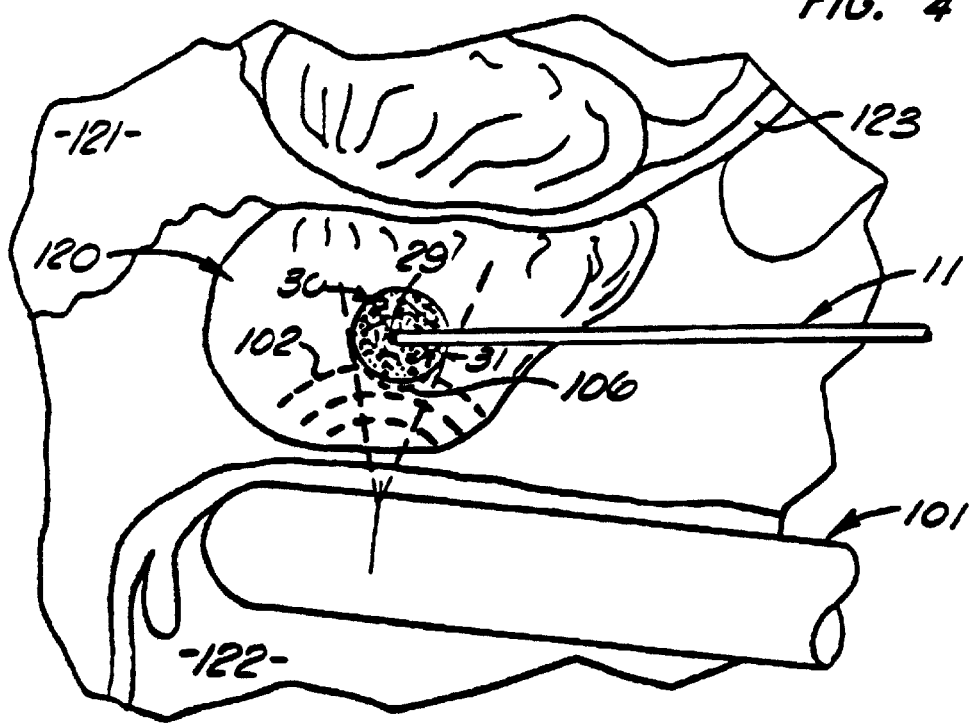
FIG. 4 is a perspective view of the probe manipulating the prostate by freezing visualized by a scanner of an ultrasound imaging system placed in the rectum.

FIG. 4 shows the function of the present invention during the freezing process. When the manipulation portion 24 of the cryoprobe 10 is positioned in the optimum location in the prostate 120, the freezing process begins. Refrigerant enters the expansion chamber 24 freezing the tissue surrounding the tip 20. The iceball 30 radiates outward from the tip 20 in approximately a spherical pattern. The pulses 102 from the TRUS scanner 101 are reflected 106 at the acoustic interface 31 between the frozen and nonfrozen tissue. The reflected pulses or echos define the position of the outer border of the iceball 30 in the image of the prostate 120 displayed by the imaging system 105. Because only a small portion of the pulses 102 are transmitted through the border 31, the imaging system 101 is unable to visualize tissue within the iceball 30. At the same time, the tip transducer 29 is unable to detect the arrival of the pulses 102 from the TRUS scanner 101.

Figure 5:
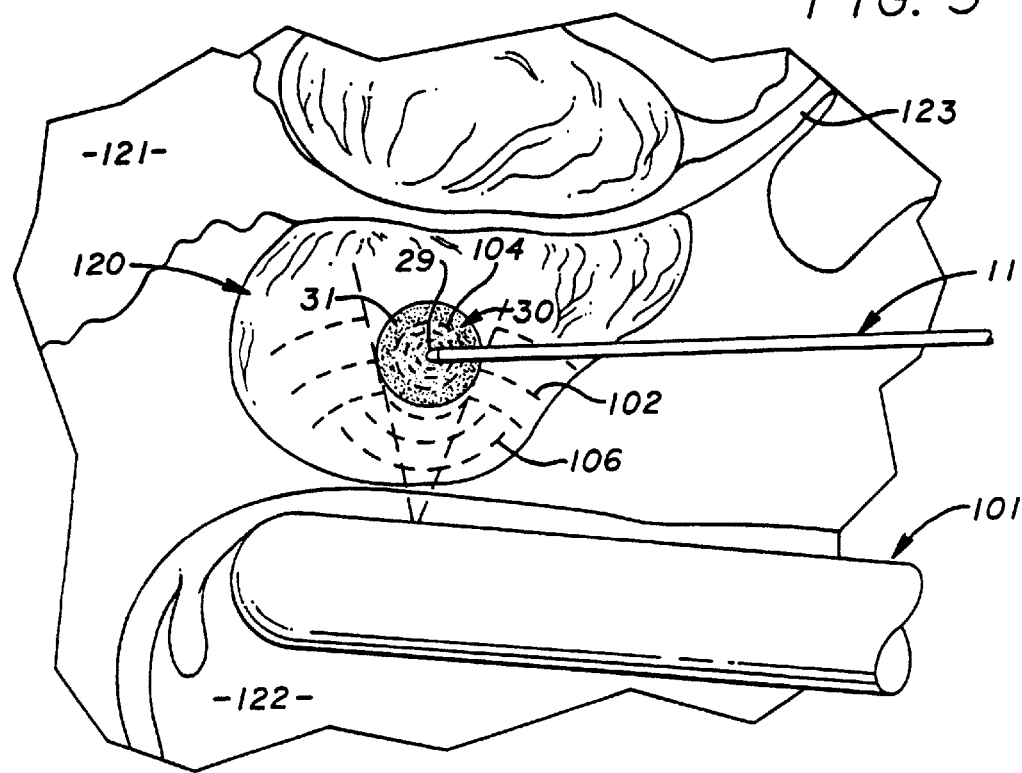
FIG. 5 is the same perspective as FIG. 4 with the probe generating ultrasound pulses at the tip during the manipulation process to enhance the visualization of the extent of the manipulation process by a scanner of an ultrasound imaging system placed in the rectum.

Without the detection of the arrival of pulses 102 by the tip transducer 29, the external electronics 110 are unable to time the generation of the ultrasound pulses 103 by the tip transducer 29. However, the freezing process immobilizes the cryoprobe, making the transit time of the pulses from the TRUS scanner 101 to the tip transducer 29 constant. Using the time constant and input from the imaging system 105 through a connecting line 111 informing the external electronics 110 of the generation of an ultrasound pulse by the scanner 101, the external electronics 110 can time the generation of ultrasound pulses 104 by the tip transducer 29 during the manipulation of the prostate, as shown in FIG. 5. Although the pulses 104 will be reflected at the inner border of the interface 31, the portion of the pulses 104 transmitted through the interface 31 will significantly enhance the visualization of the tip transducer 29 and details of tissue within the manipulated zone or iceball. Additionally, the pulses 104 reflected at the inner border of the interface 31 or echoes are detected by the transducer 29. The transit time of these pulse-echo combinations provides information to the extent of the freezing process. This information can be incorporated into the image of the iceball 30 created and displayed by the imaging system 101 to enhance visualization by defining the extent of the freezing process by the cryoprobe 10.

Figure 6:
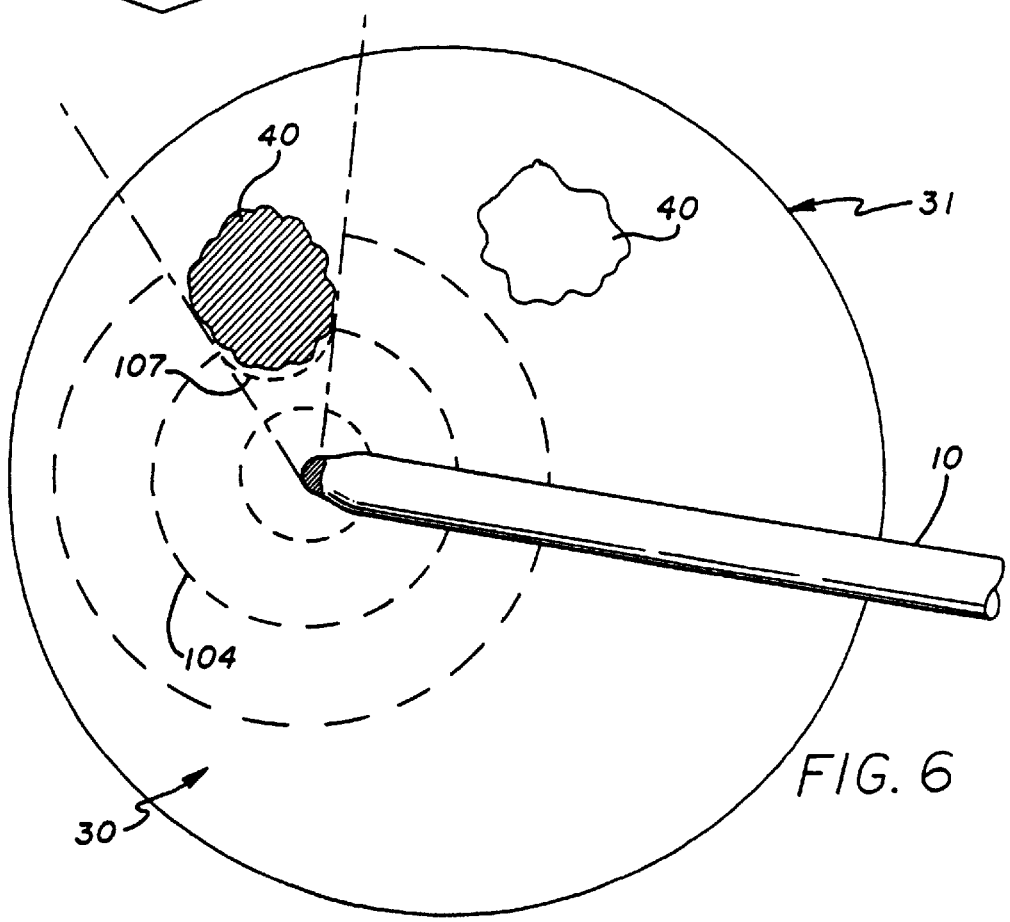
FIG. 6 is a perspective of the probe surrounded by frozen tissue during the manipulation process, generating ultrasound pulses at the probe tip that enhance the visualization of variations of the freezing process within the manipulated zone by a scanner of an ultrasound imaging system placed in the rectum.

The generation of ultrasound pulses 104 by the tip transducer 29 also enhances the visualization of details of tissue areas within the iceball 30. The reflection of ultrasound pulses from the TRUS scanner 101 at the outer border of the iceball 30 as a result of an acoustic impedance mismatch between frozen and nonfrozen tissue prevents the imaging system 105 from directly visualizing details of tissue areas within the iceball 30. As shown in FIG. 6, areas 40 of tissue that are denser or possess greater vascularization will freeze slower than surrounding tissue. As the iceball 30 radiates outward from the tip 20, these area may be encapsuled by frozen tissue without being properly frozen. The generation of ultrasound pulses by the tip transducer 29 enhances the visualization of areas 40 within the iceball 30 that would not otherwise be discernible by the imaging system 101. The surgeon or physician can then alter the freezing process by freezing a second time or extending the freezing time to guarantee that all tissue within the iceball 30 is destroyed.

The incorporation of an ultrasound transducer element in a surgical instrument in the claimed invention provides a method for performing minimally invasive surgery in a safer and more effective manner. A standard commercially available ultrasound imaging system (General Electric Medical Systems, Milwaukee, Wis., or Brauel & Kjaer, Naerum, Denmark) is used to visualize a target zone within the body. As used herein, the term "target zone" or "target zone tissue" refers to tissue within the host or body of a patient that is intended to be manipulated with the claimed method. The method for localizing the claimed invention in the target zone is facilitated by the enhancement of the visualization of the claimed invention by the imaging system as a result of ultrasound pulses generated by the transducer element in the tip of the probe.

The claimed method for manipulating target tissue of a host involves contacting the host with the scanner of an ultrasound imaging system. The scanner operates to create an image of a target zone within the host for placing the claimed surgical instrument. Accordingly, an initial step in the claimed method involves contacting the host with a scanner to visualize the target zone and surrounding tissue.

In the claimed method, the ultrasound transducer element of the probe is operatively connected with an ultrasound imaging system. The manipulation means of the probe is guided into the target zone tissue with the aid of visualization of the target zone provided by the scanner and with further image input from the ultrasound transducing element. The method involves manipulating the tissue in the target zone, and further involves manipulation of the target zone tissue with the aid of images which visualize and identify target zone tissue with reference to surrounding tissue. The effects of manipulating the target zone tissue include, but are not restricted to, destruction of the tissue, depending on the duration and intensity of the manipulation as medically indicated.

In a typical use of the claimed method, the second step of the claimed method would involve the localization of the claimed instrument in the target zone using the imaging system to guide the placement of the instrument. The ultrasound pulses generated by the transducer element, typically located on the tip of the claimed instrument, facilitate its placement by enhancing the visualization of the claimed instrument.

The third step of the claimed method typically involves the manipulation of the target zone by the claimed instrument and visualization of the extent and effectiveness of the manipulation process using the imaging system. The tip transducer element of the claimed surgical instrument is operatively connected to the ultrasound imaging system. The connection provides the means to exchange input between the transducer element and imaging system. The input allows the tip transducer element to generate ultrasound pulses during the manipulation process that enhances the extent of the manipulation process and the effect of the manipulation process in the target zone. So described, the claimed method provides a means to perform minimally invasive surgery in a manner that is safer and more effective than existing procedures.

The cryosurgical probe embodiments of the claimed surgical instrument would typically be used in a cryosurgical procedure to treat carcinoma of the prostate using the following detailed procedure, which procedure embodies the method of the invention:

Preparation of the patient

Figure 7:
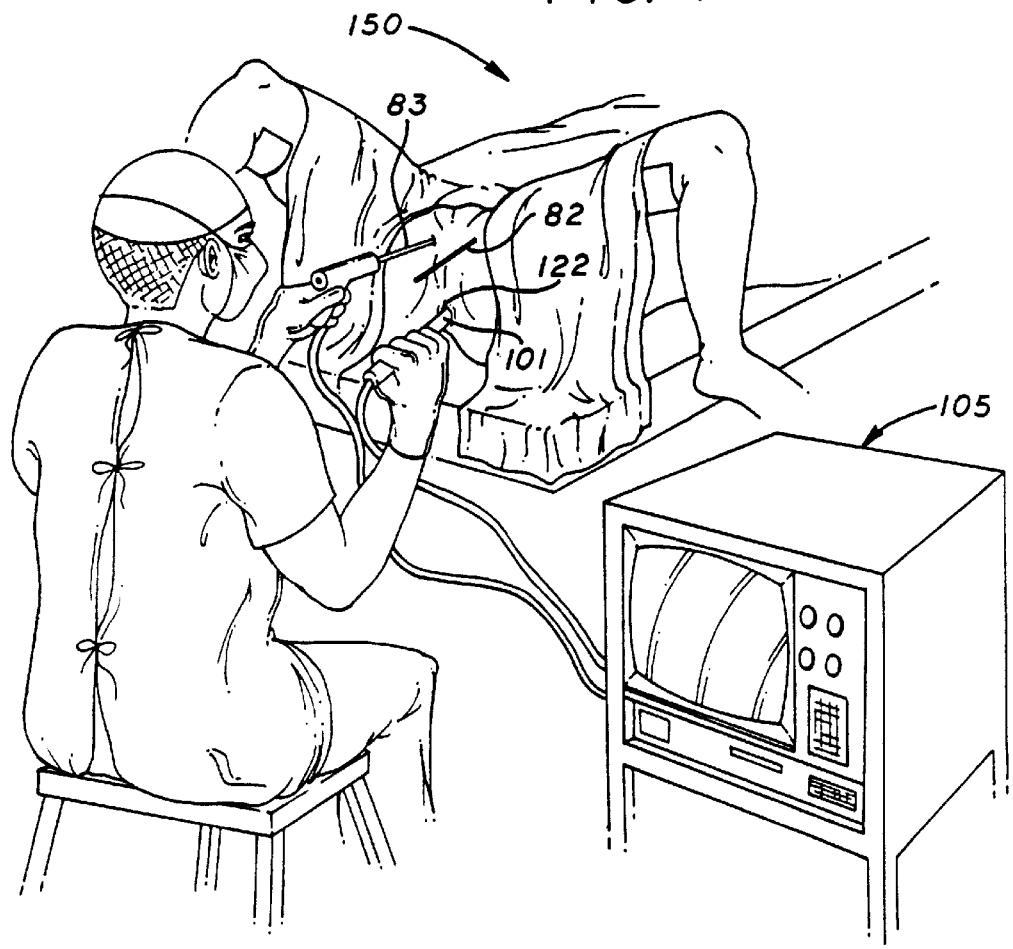
FIG. 7 is a perspective view of the surgical procedure employing the present invention and an ultrasound imaging system to treat prostate cancer using cryosurgery in a minimally invasive manner.

The patient is prepared f or sterile surgery in the dorsal lithotomy position 150 using accepted surgical procedures, as shown in FIG. 7. The scrotum is secured and the perineum, the area between the scrotum and the rectum is exposed.

A small incision approximately 4–5 mm in size is made over the pubic bone. At the same time, a cystoscope is placed in the bladder through the urethra. The cystoscope allows the surgeon to visualize the placement of a trocar through a suprapubic incision into the bladder. A Foley catheter is inserted through the trocar into the lumen of the bladder and the balloon of the catheter inflated with approximately 10 cc of fluid.

A guidewire is placed through the cystoscope into the bladder and the cystoscope removed leaving the guidewire in place. A Coude tipped Foley catheter is inserted into the bladder over the guidewire and the balloon of the catheter is inflated with 10 cc of water.

An ultrasound scanner 101, operating at approximately 7.5 MHZ, is inserted in th e rectum 122 and the prostate 120 and surrounding tissue is displayed by an ultrasound imaging system 105, a process described as transrectal ultrasonography or TRUS. Size of the prostate 120, which contains the target zones, is estimated by taking measurements of length, width and height from the ultrasound image. These measurements are used to calculate prostatic volume. The volume is used to determine the number of cryoprobes 10 required to manipulate the prostate 120, i.e. freeze the prostate 120, as well as the number of freeze cycles that will be required to complete the surgical procedure. Cryoprobes typically freeze tissue in a zone 1 centimeter in radius around the tip of the probe. If the prostate 120 is 4 centimeters long, two freezing cycles would be required, one for the proximal 2 centimeters and another for the distal 2 centimeters.

Figure 8:
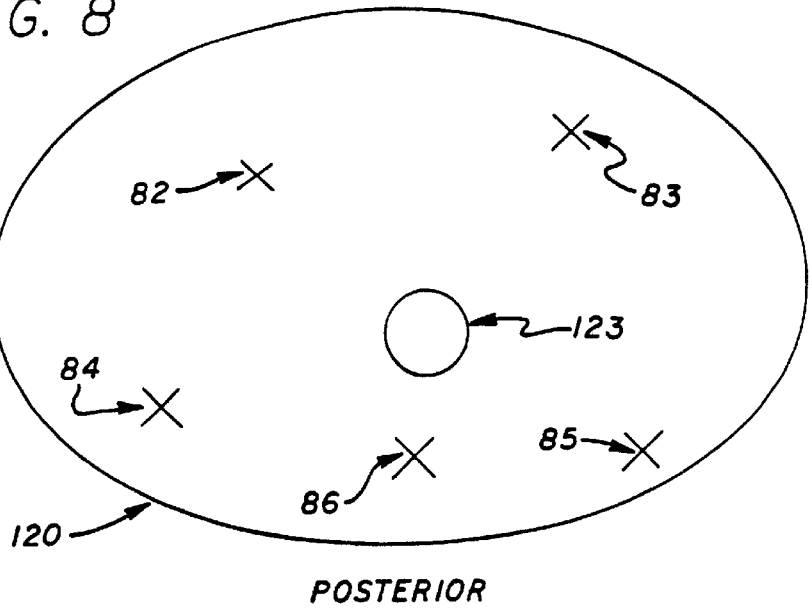
FIG. 8 is a cross-sectional view of the prostate showing the desired position of the placement of the probes within the prostate for the treatment of prostate cancer using cryosurgery in a minimally invasive manner.

Insertion of claimed CryoProbes,

Depending on prostatic volume, four or five of the present cryoprobes 10 would be placed in the prostate 120 in positions shown in FIG. 8 following the described procedure. A locating needle 82 is inserted percutaneously via the perineum into the prostate 120. The first locating needle 82 is placed in the anterior aspect of the prostate 120 on the left or right side. The locating needle is placed up to within 0.5 cm of the proximal portion of the prostatic capsule. The TRUS scanner 101 is used to properly position the needles in the prostate 120.

Following the placement of the locating needles in the left 82 and right 83 anterior aspect of the prostate 120, a third 84 and fourth 85 needles are placed in the left and right posterior aspect of the prostate. If required, a fifth needle 86 is placed underneath the urethra 123. All needles are placed approximately 0.5 cm from the proximal prostatic capsule as determined by TRUS. The use of needles as a first step is to minimize the trauma of multiple attempts of locating the proper position, that is, the target zones within the prostate 120 for placing the cryoprobes.

The next step in the procedure is to replace the needles with the claimed surgical instrument, the cryoprobes. This involves guiding the placement of the manipulation means into the target zone with the aid of the image created by the ultrasound imaging system and with the aid of pulses generated by the ultrasound transducer in the cryoprobe. The pulses generated by the transducer enhance the ultrasound image of the location of the manipulation means within the target tissue, as the manipulation means is guided toward the target zone. Small puncture wounds are made around the needles before removal to facilitate the passage of the cryoprobes through the skin. The cryoprobes are inserted in the same order as the locating needles.

During the placement of the cryoprobes, a catheter is inserted over the guidewire through the urethra into the bladder. This catheter controls a continuous flow of warm water (30–36° C.) through the urethra, keeping it warm and preventing damage to the urethral wall. After establishing a flow of warm water through the urethra, the temperature of each cryoprobe tip is reduced to approximately −20° C., freezing the tissue surrounding the cryoprobe tip 20. This immobilizes the cryoprobe, locking it in position and preventing accidental displacement of the cryoprobe. When all cryoprobes are properly located and frozen in good position, approximately 0.5 cm from the prostatic capsule as displayed by the TRUS image, the freezing of the prostate is started.

The freezing process begins by reducing the temperature of the anterior cryoprobe tips to below −180° C. The transit time between the tip transducer 29 and the TRUS scanner 101 is measured at the start of the freezing process. The progression of freezing of prostate tissue is visualized using TRUS with the aid of pulses generated by the ultrasound transducer 29 of the cryoprobe 10. Accordingly, the method of the invention achieves concurrently with manipulation, an ultrasound image that visualizes and identifies tissue within the target destroyed by the step of manipulating the tissue in said target zone. The outer border of the target zone or iceball 30, the acoustic interface between frozen and non-frozen tissue, is displayed as an arc radiating outward from the cryoprobe tip 24 in the display of the imaging system. Areas 40 of nonuniform freezing within the iceball 30 appear as darker than surrounding tissue as a result of the reflection of ultrasound energy at the surface of the nonuniformity. Detection of the reflected energy or echos 107 of the pulses 104 generated by the tip transducer 29 is input into the imaging system 105 through the connecting line 111 to enhance the details of the extent of the freezing process and details of the uniformity of freezing within the iceball 30.

As the freezing process continues, it spreads through the anterior portion of the prostate and progresses towards the posterior portion of the prostate. The temperature of the posterior cryoprobe tips is reduced to below −180° C. as the freezing process continues into the posterior prostate. Finally, if present, the temperature of the fifth cryoprobe tip underneath the urethra is reduced to below −180° C. and the entire prostate is frozen.

Damage to tissues and organs bordering the prostate as a result of the freezing process is a major concern for the physician or surgeon. The urethra is protected from damage during the freezing process by providing heat to the urethral wall. The anterior portion of the prostate is surrounded by loose fat which acts to insulate the prostate from other organs and tissues. The posterior portion of the prostate rests on the rectum separated from the prostate by a thin layer of perirectal fat. The extent of the freezing process is carefully monitored in accordance with the claimed method. The freezing process is not allowed to progress beyond the perirectal fat lest damage to the rectal wall occur.

Upon termination of the freezing process, a thaw cycle is started. The thaw cycle is accomplished by pumping heated gas through the cryoprobe, increasing the temperature at the cryoprobe tip and the surrounding tissue. When the tissue surrounding the cryoprobe tips sufficiently thaws to loosen the probes, they are removed and the operation is completed.

Although the present invention has been described in considerable detail with regards to certain preferred embodiments, other embodiments are possible. For example, the claimed surgical instrument can be embodied as a surgical probe incorporating a microwave antenna for manipulating tissue and an ultrasound transducer for precisely placing the probe in a breast tumor under ultrasound imaging guidance. With the portion of the probe containing the antenna in the center of the tumor, microwave energy can be delivered to the tissue surrounding the antenna. This heats the surrounding tissue causing it to die, thus destroying the tumor. Positioning the probe is critical to ensure that the heat zone encompasses the entire tumor, but does not include healthy tissue or organs surrounding the tumor.

At the same time, pulses from the transducer enhance the visualization of tissue within the heat zone that are not discernible by ultrasound imaging from outside the zone due to reflection, absorption, refraction, or diffraction of the imaging pulses outside the zone of manipulated tissue. The heating of the tumor surrounding the probe depends on the vascularization of the tissue. Areas more highly vascularized will heat slower than areas less vascularized. When scanned with an ultrasound imaging system from outside the heated zone, areas more highly vascularized may be shielded from the imaging system by areas less vascularized that heat quicker. The inability to identify highly vascularized tissue areas may lead the operator to assume tumor destruction when areas within the tumor are still viable. The pulses generated by the ultrasound transducer on the probe at the center of the heated zone enhance the visualization of non-uniform heating, revealing areas within the zone that had not reached sufficient temperature to destroy the tissue.

Having thus disclosed exemplary embodiments of the present invention, it should be noted by those skilled in the art that the disclosures herein are exemplary only and that various other alternatives, adaptions, and modifications may be made within the scope of the present invention. Accordingly, the present invention is only limited by the following claims.

What is claimed is:

1. A medical device for use with an ultrasound scanner which generates an incident ultrasound pulse and generates a timing signal, said medical device comprising:

a probe adapted for insertion into a patient, said probe comprising a manipulator for manipulating tissue within a zone of manipulation; and an ultrasound transducer disposed within said zone of manipulation; and electronics coupled to said transducer, said electronics configured to receive the timing signal from the ultrasound scanner and configured to control said transducer such that when a signal level of said incident ultrasound pulse falls below a level at which said transducer may detect said incident ultrasound pulse, said electronics drives said transducer to generate a timed ultrasound pulse based on the timing signal.

2. The medical device of claim 1, wherein said transducer is located in a vicinity of a tip of said probe.

3. The medical device of claim 1, wherein said transducer is in a distal portion of said probe.

4. The medical device of claim 3, wherein said manipulator removes energy from the tissue.

5. The medical device of claim 3, wherein said manipulator adds energy to the tissue.

6. The medical device of claim 3, wherein said manipulator destroys the tissue.

7. The medical device of claim 3, further comprising an imaging system for displaying an image derived from said responsive radiated signal.

8. A method of determining a measure of freezing of tissue comprising the steps of:

disposing a transducer within an area of tissue;

freezing the tissue around said transducer within said area of tissue;

receiving an incident ultrasound pulse at a transducer disposed within said area of tissue during said step of freezing; and responding to said incident radiated signal by transmission of a responsive ultrasound pulse.

9. The method of claim 8, further comprising the step of continuing to transmit an ultrasound pulse from said transducer when said incident radiated signal is no longer detectable by said transducer.

10. The method of claim 8, further comprising the steps of:

receiving said responsive ultrasound pulse at an imaging device; and displaying a real-time image of said area of tissue during said step of freezing.

11. A medical device comprising:

a probe adapted for insertion into a patient, said probe comprising a cryogenic tip for freezing tissue in a predetermined area; and a transducer on said probe and disposed within said predetermined area, wherein said transducer responds to receipt of an incident radiated signal by generation of a responsive radiated signal so that an extent of tissue freezing may be monitored and responds to receipt of an external timing signal by generation of said responsive radiated signal so that said extent of tissue manipulation may be monitored if a signal strength of said incident radiated signal falls below a detectable level.

12. A medical device comprising:

a cryoprobe configured to freeze an area of tissue;

a transducer attached to said cryoprobe such that said transducer is inserted into and removed from said area of the tissue with said probe; and electronics coupled to said transducer and configured to control said transducer such that said transducer responds to receipt of an incident radiated signal by generation of a responsive radiated signal and responds to receipt of an external timing signal by generation of said responsive radiated signal if a signal strength of said incident radiated signal falls below a predetermined level.

13. A medical device comprising:

a probe adapted for insertion into a patient, said probe comprising a cryogenic manipulator for freezing tissue within a zone of manipulation; and a transducer on said probe and disposed within said zone of manipulation, and including electronics to drive said transducer to respond to receipt of an incident radiated signal by generation of a responsive radiated signal to aid in visualization of tissue freezing and to respond to receipt of an external timing signal by generation of said responsive radiated signal so that said visualization of tissue freezing may be monitored if a signal strength of said incident radiated signal falls below a threshold level.

14. The medical device of claim 13, wherein said transducer is located at a tip of said probe.

15. The medical device of claim 14, further comprising an ultrasound scanner configured to transmit said incident radiated signal and receive said responsive radiated signal.

16. The medical device of claim 15, wherein said scanner comprises an imaging system for displaying an image derived from said responsive radiated signal.

17. The medical device of claim 15, further comprising electronics coupled to said transducer configured to receive a timing input from said scanner so that when a signal level of said incident radiated signal falls below a level at which said transducer may detect said incident radiated signal, said electronics drives said transducer to generate a timed radiated signal based on said timing input.

* * * * *